US00PP14369P39

(12) United States Plant Patent
Friday

(10) Patent No.: US PP14,369 P3
(45) Date of Patent: Dec. 16, 2003

(54) PEACH TREE NAMED 'P.F. 14 NEW JERSEY'

(50) Latin Name: *Prunus persica*
Varietal Denomination: P.F. 14 New Jersey

(75) Inventor: Paul Jan Friday, Coloma, MI (US)

(73) Assignee: Paul J. Friday, Coloma, MI (US)

( * ) Notice: Subject to any disclaimer, the term of this patent is extended or adjusted under 35 U.S.C. 154(b) by 0 days.

(21) Appl. No.: 10/051,941

(22) Filed: Jan. 22, 2002

(65) Prior Publication Data

US 2003/0140387 P1 Jul. 24, 2003

(51) Int. Cl.[7] ..... A01H 5/00

(52) U.S. Cl. ..... Plt./198
(58) Field of Search ..... Plt./198

*Primary Examiner*—Bruce R. Campell
*Assistant Examiner*—W C Haas

(57) ABSTRACT

A new and distinct variety of peach. *Prunus persica,* tree having the following unique combination of desirable features:

1. Producing a very firm fruit having a resilient flesh texture.
2. Blossoms are non-showy when in full bloom.
3. A substantially spherical fruit with yellow flesh having red mottling.
4. A mid-season peach variety that matures after 'Redhaven' (unpatented) and which has good storage and shelf life.

1 Drawing Sheet

Botanical classification: *Prunus persica.*

ORIGIN OF VARIETY

The new peach tree (hereinafter referred to as the 'P.F. 14 New Jersey' peach tree) was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 14 New Jersey', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom.

The blossoms of the present peach tree at full bloom may be characterized as being non-showy. More specifically, the blossoms of the present peach tree have angularly spaced five-blossom petals projecting upwardly at an inclined angle so as to form a blossom having a diameter of about ¾" measured across the blossoms. The typical non-showy blossom as exemplified for example by the 'Redhaven' (unpatented) peach has five (5) radially extending and angularly spaced petals projecting upwardly at a relatively steep inclined angle so that the diametrical measurement across the outer edges of the petals is about ½".

The flesh of the fruit of the present peach tree is firm and is yellow with a minimum of red around the pit.

The skin is smooth and is of dark red color over almost 100 percent (100%) of its surface at full maturity. The fruit is large with an average diameter of 2¾".

It is noteworthy that the fruit of this tree is further characterized as having smooth, gently rounded cheeks at the blossom end of the fruit. These protrude to form fruit surfaces higher than the blossom point. This characteristic reduces fruit damage in harvest, shipping and storage, by reducing the exposure of and damage to the apical blossom protrusion in handling. Thus breaching of the skin and formation of an entry point for microorganisms which cause rot in many other commercially important peach varieties harvested in the same production period is avoided in this fruit.

The fruit has a firm flesh and may be described as resilient to the extent that the flesh is yieldable and restorable to its original state when subjected to impact forces, which may cause permanent deformities in peaches of the commercial varieties. The firmness of the fruit facilitates handling and packaging of the peaches without damaging the same for shipment. This results in less spoilage and also increases the shelf life.

BRIEF DESCRIPTION OF THE PHOTOGRAPHS

The accompanying photographic illustrations of the new variety show the following:

The top photograph depicts well-rounded fruit showing an unpronounced suture and a well-rounded blossom end. One specimen of the fruit is bisected at a ninety-degree angle to the plane of the suture with the stone retained in half showing its freestone characteristic and clear yellow flesh and a minimum of red around the pit. A tape measure is present indicating the large size of the fruit.

The bottom photograph depicts leaves of medium length and width, having notably very fine serrated margins. A tape measure is present, demonstrating the medium size of the leaves. Whole fruit is also present.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. 14 New Jersey'.

Tree:
- *Age.*—Ten (10) years.
- *Height.*—Unpruned 15'.
- *Width.*—Unpruned 12'.
- *Size.*—Medium.
- *Vigor.*—Medium.
- *Density.*—Medium — moderate pruning required.
- *Form.*—Moderately spreading.
- *Production.*—Good in regions of moderate climate — somewhat bud-tender in colder climates.
- *Bearer.*—Consistent in regions of moderate climate.
- *Disease resistance to bacterial leaf and fruit spot.*—Very good.

Trunk:
- *Bark.*—Gray (421).
- *Size.*—Medium to stocky.
- *Surface.*—Smooth.
- *Diameter.*—3½"–24" above the ground at 10 years of age.

Branches:
- *Size.*—Medium — 1½" to 1¾" at trunk union.
- *Surface.*—Smooth to medium.
- *Lenticels per square inch on branch.*—Usually ten (10).
- *Lenticel color on branch.*—406.
- *Crotch angles.*—About 60 degrees.
- *Branch color.*—Gray (420).

Leaves:
- *Size.*—5¼" long — 1½" wide.
- *Color.*—Top of leaf 575, bottom of leaf 363.
- *Form.*—Lanceolate — pointed.
- *Thickness.*—Medium.
- *Texture.*—Glabrous.
- *Margin.*—Finely serrated.
- *Petiole.*—Length, 5/16" — medium thickness.
- *Gland.*—1 to 5 small on the petiole and basal part of the leaf.
- *Gland color.*—Yellow (101) during the growing season, and red in the fall.
- *Gland shape.*—Oval.

Flower buds:
- *Size.*—⅜" long, ¼" wide.
- *Shape.*—Cupped.
- *Color.*—223.

Flowers:
- *Blooming period.*—May 3, 2001 to May 6, 2001.
- *Size of petals.*—⅜" long, ¼" wide.
- *Shape of petals.*—Cupped.
- *Sepal size.*—⅛" long, 1/16" wide.
- *Sepal shape.*—Cupped.
- *Sepal color.*—366.
- *Number of anthers.*—32.
- *Anther color.*—469.
- *Number of stamens.*—32.
- *Stamen length.*—⅜".
- *Stamen color.*—413.
- *Pistil length.*—¼".
- *Pistil color.*—102.
- *Pollen.*—Present, self-fertilizing.
- *Flower and petal color.*—230.
- *Petals per cluster.*—Five (5).
- *Flowers per cluster.*—Usually two (2) to three (3).
- *Fragrance.*—Very slight.

Fruit:
- *Maturity when described.*—Firm ripe.
- *Date of first picking.*—Aug. 14, 2001.
- *Date of last picking.*—Aug. 20, 2001.
- *Size.*—Large sphere — Average diameter 2¾".
- *Form.*—Oblate spherical.
- *Suture.*—Medium.
- *Weight.*—Average 8 oz.

Skin:
- *Thickness.*—Medium.
- *Texture.*—Tough, tenacious to skin.
- *Tendency to crack.*—None.
- *Down.*—Moderate to little.
- *Color.*—Almost entirely red (varying in shades from 221 to 222).

Flesh:
- *Texture.*—Firm.
- *Ripens.*—Evenly.
- *Flavor.*—Excellent.
- *Aroma.*—Pleasant.
- *Eating quality.*—Very good.
- *Color.*—Dark yellow (129).
- *Color around pit cavity.*—Red (213).

Stone:
- *Type.*—Very freestone.
- *Size.*—Average length — 1½". Average width — 1". Average thickness — ¾".
- *Form.*—Ovid.
- *Base.*—Straight.
- *Apex.*—Pointed.
- *Sides.*—Unequal.
- *Surface.*—Furrowed.
- *Color.*—Reddish brown (159).
- *Tendency to crack.*—About 3%.
- *Kernel.*—11/16" long, 7/16" wide, 1/32" thick.

Use: Desert.

Shipping quality: Good.

Keeping quality: Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree, substantially as herein illustrated and described.

* * * * *

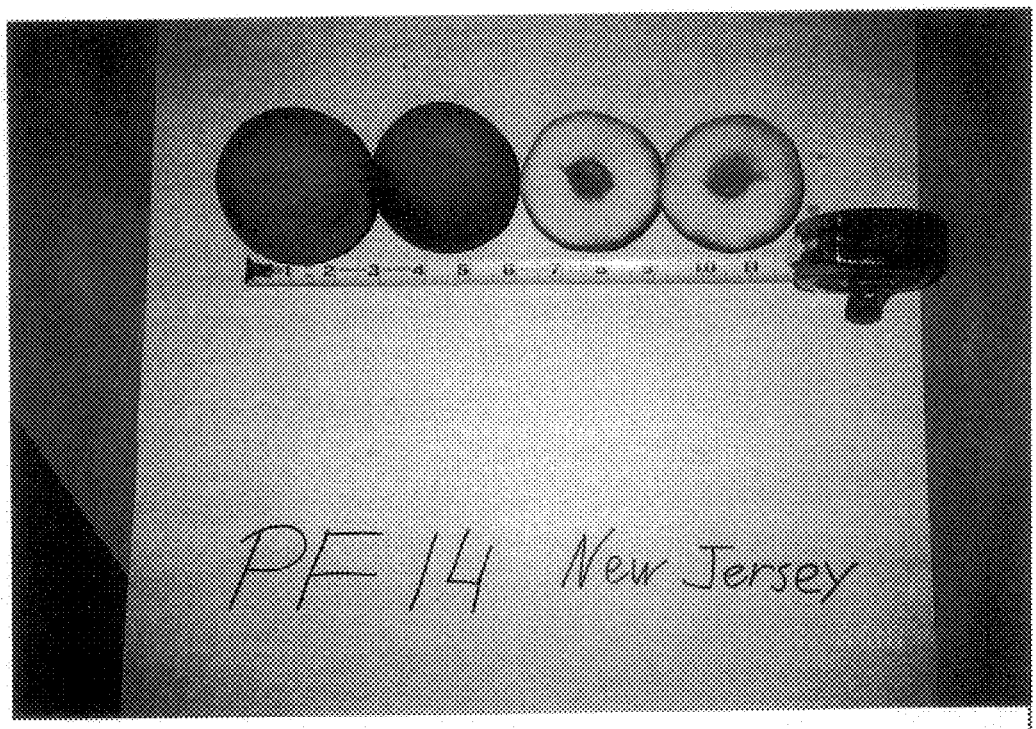
PF 14 New Jersey
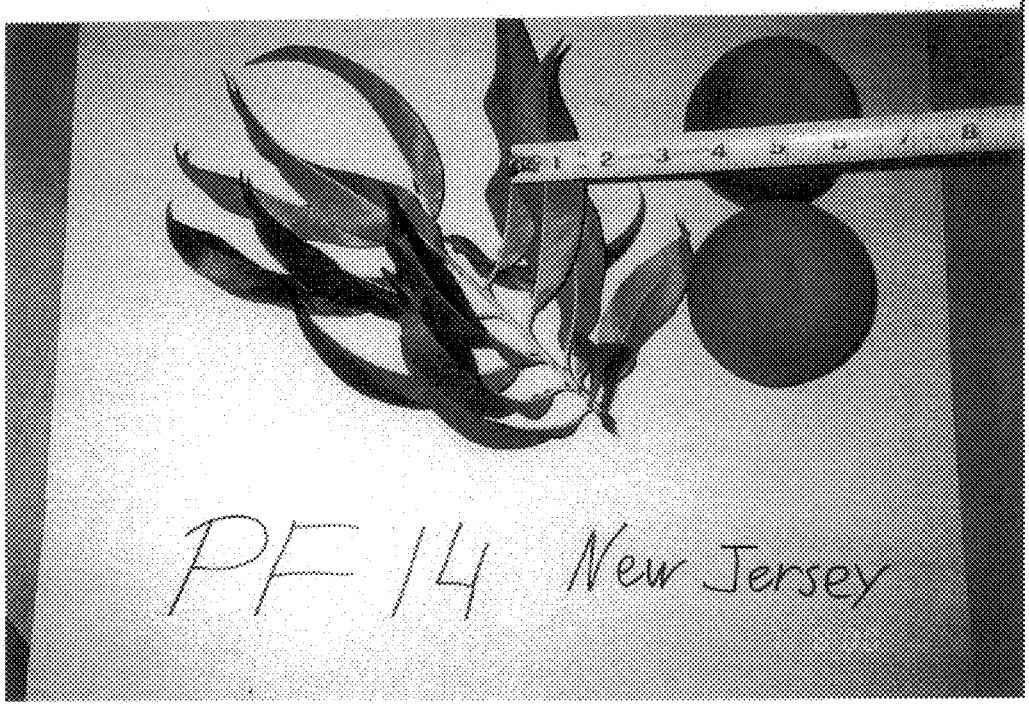
PF 14 New Jersey